US00PP20350P2

(12) United States Plant Patent
Noordhuis

(10) Patent No.: US PP20,350 P2
(45) Date of Patent: Sep. 22, 2009

(54) ***EUCOMIS* PLANT NAMED 'EXC 051'**

(50) Latin Name: *Eucomis hybrida*
Varietal Denomination: EXC 051

(75) Inventor: Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 0 days.

(21) Appl. No.: 12/074,419

(22) Filed: Mar. 3, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Eucomis* plant named 'EXC 051', characterized by its compact and outwardly arching plant habit with upright, strong and relatively short inflorescence stalks; freely flowering habit; and purple-colored flowers with white-colored centers.

2 Drawing Sheets

Botanical designation: *Eucomis hybrida.*
Cultivar denomination: 'EXC 051'.

BACKGROUND OF THE INVENTION

The present invention relates to a new and distinct cultivar of *Eucomis,* botanically known as *Eucomis hybrida* and hereinafter referred to by the name 'EXC 051'.

The new *Eucomis* is a product of a planned breeding program conducted by the Inventor in Boijl, The Netherlands. The objective of the breeding program is to create new compact *Eucomis* cultivars with unique and bright flower colors.

The new *Eucomis* originated from a cross-pollination made by the Inventor in 2004 in Boijl, The Netherlands, of two unnamed selections of *Eucomis hybrida,* not patented. The new *Eucomis* was discovered and selected by the Inventor as a flowering plant from within the progeny of the stated cross-pollination in a controlled environment in Boijl, The Netherlands in 2005.

Asexual reproduction of the new *Eucomis* by bulb divisions in a controlled environment in Boijl, The Netherlands since the summer of 2006, has shown that the unique features of this new *Eucomis* are stable and reproduced true to type in successive generations.

SUMMARY OF THE INVENTION

The cultivar EXC 051 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'EXC 051'. These characteristics in combination distinguish 'EXC 051' as a new and distinct cultivar of *Eucomis:*

1. Compact and outwardly arching plant habit with upright, strong and relatively short inflorescence stalks.
2. Freely flowering habit.
3. Purple-colored flowers with white-colored centers.

Plants of the new *Eucomis* differ from plants of the parent selections in the following characteristics:

1. Plants of the new *Eucomis* have shorter inflorescence stalks than plants of the parent selections.
2. Plants of the new *Eucomis* and the parent selections differ in flower color as plants of the parent selections have light pink-colored flowers.

Plants of the new *Eucomis* can be compared to plants of the cultivar Sparkling Burgundy, not patented. In side-by-side comparisons conducted in Boijl, The Netherlands, plants of the new *Eucomis* and the cultivar Sparkling Burgundy differed in the following characteristics:

1. Plants of the new *Eucomis* were more compact than plants of the cultivar Sparkling Burgundy.
2. Plants of the new *Eucomis* were not as vigorous as plants of the cultivar Sparkling Burgundy.
3. Plants of the new *Eucomis* had shorter inflorescence stalks than plants of the cultivar Sparkling Burgundy.
4. Plants of the new *Eucomis* had smaller flowers than plants of the cultivar Sparkling Burgundy.
5. Plants of the new *Eucomis* and the cultivar Sparkling Burgundy differed in flower color as plants of the cultivar Sparkling Burgundy had pink-colored flowers.

BRIEF DESCRIPTION OF THE PHOTOGRAPHS

The accompanying colored photographs illustrate the overall appearance of the new *Eucomis,* showing the colors as true as it is reasonably possible to obtain in colored reproductions of this type. Colors in the photographs may differ slightly from the color values cited in the detailed botanical description which accurately describe the colors of the new *Eucomis.*

The photograph on the first sheet comprises a side perspective view of a typical flowering plant of 'EXC 051'.

The photograph on the second sheet is a close-up view of typical flowers of 'EXC 051'.

DETAILED BOTANICAL DESCRIPTION

The aforementioned photographs and following observations, measurements and values describe plants grown in Boijl, The Netherlands, under commercial practice during the summer in an outdoor nursery. Plants had been growing for about a year when the photographs and description were taken. During the production of the plants, day temperatures ranged from 15° C. to 30° C. and night temperatures ranged from 10° C. to 15° C. In the following description, color references are made to The Royal Horticultural Society Colour Chart, 2001 Edition, except where general terms of ordinary dictionary significance are used.

Botanical classification: *Eucomis hybrida* cultivar EXC 051.

Parentage:

*Female, or seed, parent.*—Unnamed selection of *Eucomis hybrida,* not patented.

*Male, or pollen, parent.*—Unnamed selection of *Eucomis hybrida,* not patented.

Propagation:

*Type.*—By bulb divisions.

*Time to initiate roots.*—About 20 to 30 days at 15° C. to 30° C.

*Root description.*—Fleshy; light brown to white in color.

*Rooting habit.*—Freely branching.

Plant description:

*Plant form/habit.*—Herbaceous flowering perennial plant. Compact plant habit with outwardly arching foliage with upright, strong and relatively short inflorescence stalks. Flowering stems and leaves basal; moderately vigorous growth habit.

*Plant height* (*soil level to top of inflorescences*).—About 50 cm.

*Plant width* (*spread*).—About 20 cm.

Foliage description:

*Arrangement/form.*—Basal rosette, simple, sessile.

*Length.*—About 35 cm to 40 cm.

*Width.*—About 3 cm to 5 cm.

*Shape.*—Lanceolate.

*Apex.*—Acute.

*Base.*—Decurrent.

*Margin.*—Entire.

*Texture, upper and lower surfaces.*—Smooth, glabrous.

*Venation pattern.*—Parallel.

*Color.*—Developing and fully developed leaves, upper surface: Close to 146B, at the margins, 59A; venation, 146D. Developing and fully developed leaves, lower surface: Close to 146C, at the margins, 59A; midvein, 181A, and primary veins, 147A.

Flower description:

*Flower type/habit.*—Numerous single funnelform flowers with fused perianth arranged on terminal racemes; flowers face outwardly. Perianth segments separate. Freely flowering habit; about 60 to 70 flowers per raceme.

*Fragrance.*—None detected.

*Natural flowering season.*—Continuously flowering from June to mid-September in The Netherlands.

*Postproduction longevity.*—Flowers last about 15 to 20 days on the plant; flowers not persistent.

*Flower buds.*—Height: About 8 mm to 10 mm. Diameter: About 5 mm. Shape: Elliptic. Color: Close to 79B.

*Inflorescence height.*—About 30 cm.

*Inflorescence diameter.*—About 5 cm to 7 cm.

*Flower diameter.*—About 2.5 cm.

*Flower depth.*—About 8 mm.

*Petals.*—Arrangement: Six petals arranged in a single whorl. Length: About 8 mm. Width: About 4 mm. Shape: Ovate. Apex: Acuminate. Margin: Entire. Texture, upper and lower surfaces: Smooth, glabrous. Color: When opening, upper surface: Close to 77A. When opening, lower surface: Close to 79C. Fully opened, upper surface: Close to 79B; towards the center, close to 155A. Fully opened, lower surface: Close to 79A.

*Flower bracts.*—Quantity/arrangement: About 10 to 15 leafy bracts at the apex of the inflorescence stalk. Length: About 3 cm to 4 cm. Width: About 1 cm. Texture, upper and lowers surfaces: Smooth, glabrous. Color, upper and lower surfaces: Close to 146B, at the margins, 71A.

*Pedicels.*—Length: About 1.5 cm to 2 cm. Diameter: About 1 mm. Angle: Erect. Strength: Strong. Texture: Smooth, glabrous. Color: Close to N79B.

*Reproductive organs.*—Stamens: Quantity per flower: Typically six. Filament length: About 7 mm. Filament color: Towards the base, close to 155A; towards the apex, close to 77B. Anther shape: Oval. Anther length: About 2 mm. Anther color: Close to 7B. Pollen amount: Scarce. Pollen color: Close to 5D. Pistils: Quantity per flower: One. Pistil length: About 8 mm. Style length: About 5 mm. Style color: Close to N79A. Ovary color: Close to N79A.

*Seeds/fruits.*—Seed and fruit development have not been observed on plants of the new *Eucomis.*

Disease/pest resistance: Plants of the new *Eucomis* have not been noted to be resistant to pathogens and pests common to *Eucomis.*

Garden performance: Plants of the new *Eucomis* have been observed to have good garden performance and to tolerate rain, wind and temperatures from −10° C. to 35° C.

It is claimed:

1. A new and distinct *Eucomis* plant named 'EXC 051' as illustrated and described.

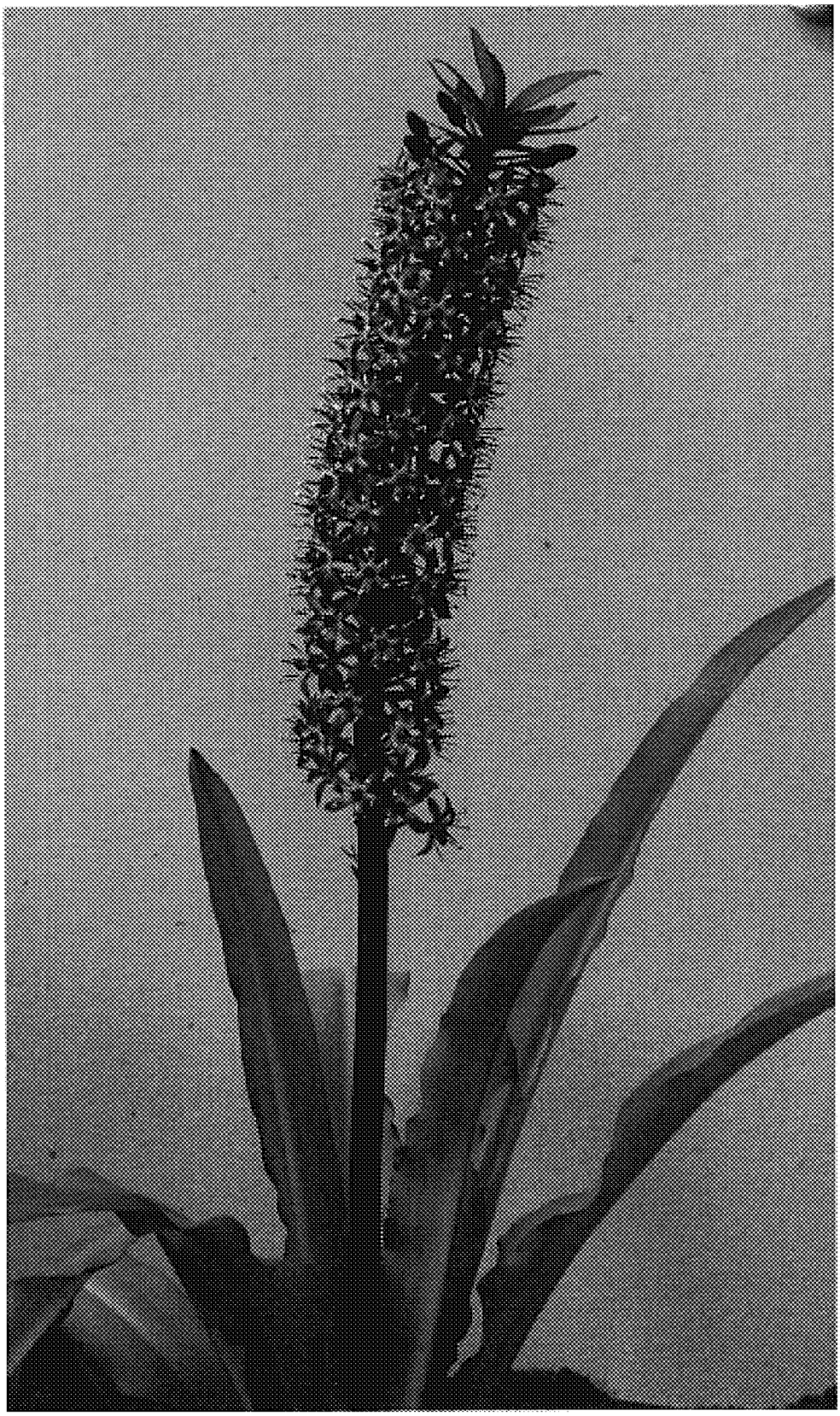

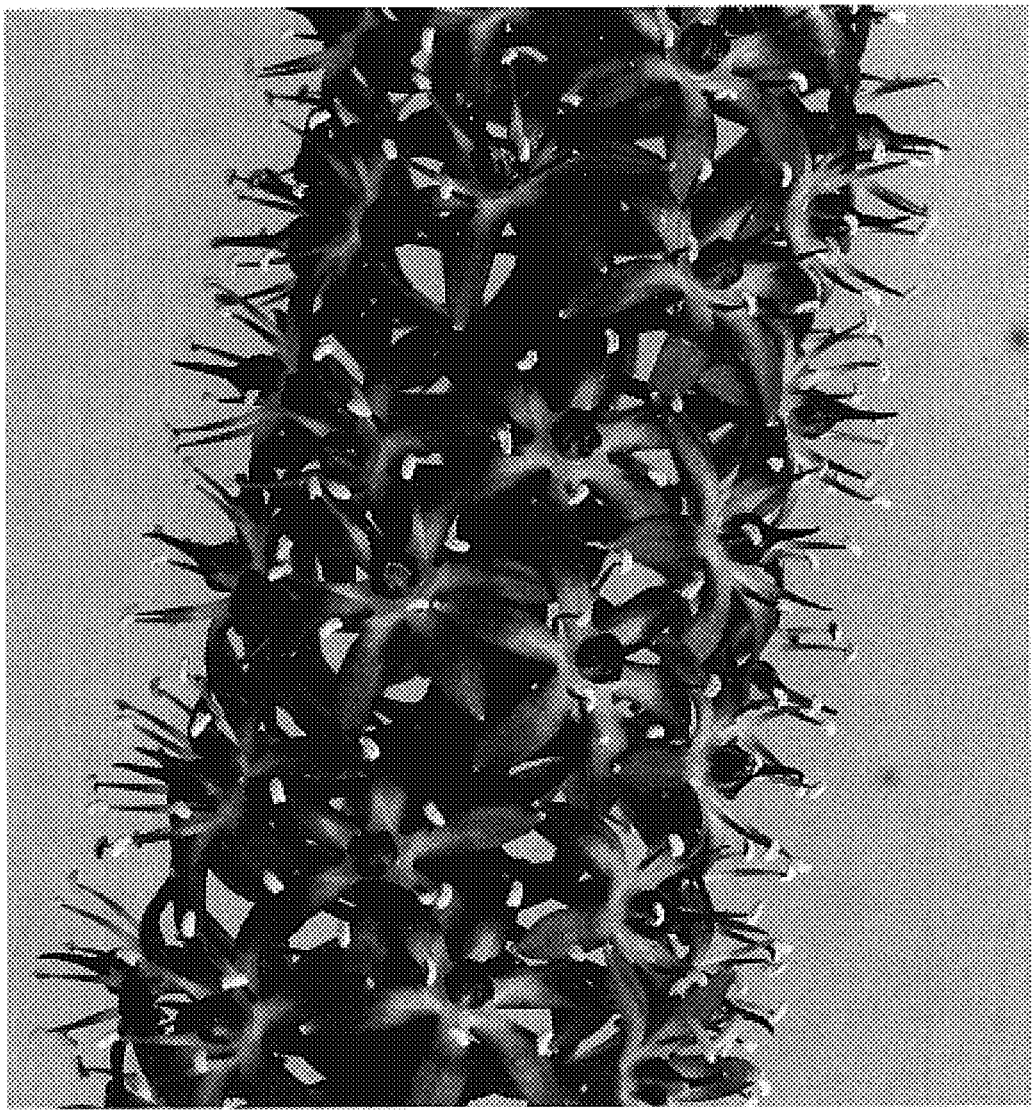

* * * * *